(12) United States Patent
Yanagisawa et al.

(10) Patent No.: US 7,041,843 B2
(45) Date of Patent: May 9, 2006

(54) PREPARATION OF SULFIDE CHAIN-BEARING ORGANOSILICON COMPOUNDS

(75) Inventors: Hideyoshi Yanagisawa, Gunma-ken (JP); Masaaki Yamaya, Gunma-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 210 days.

(21) Appl. No.: 10/382,540

(22) Filed: Mar. 7, 2003

(65) Prior Publication Data
US 2003/0176719 A1 Sep. 18, 2003

(30) Foreign Application Priority Data
Mar. 8, 2002 (JP) .............................. 2002-062900

(51) Int. Cl.
C07F 7/04 (2006.01)
C07F 7/08 (2006.01)

(52) U.S. Cl. ........................................ 556/427; 528/30
(58) Field of Classification Search ................ 556/427; 528/30
See application file for complete search history.

(56) References Cited

U.S. PATENT DOCUMENTS

| 4,507,490 A | 3/1985 | Panster |
| 5,399,739 A | 3/1995 | French et al. |
| 5,405,985 A | 4/1995 | Parker et al. |
| 5,440,064 A | 8/1995 | Agostini et al. |
| 5,466,848 A | 11/1995 | Childress |
| 5,468,893 A | 11/1995 | Parker et al. |
| 5,489,701 A | 2/1996 | Childress et al. |
| 5,583,245 A * | 12/1996 | Parker et al. ................ 556/427 |
| 5,596,116 A | 1/1997 | Childress et al. |
| 5,663,358 A | 9/1997 | Cohen et al. |
| 5,663,395 A | 9/1997 | Göbel et al. |
| 5,663,396 A | 9/1997 | Müsleve et al. |
| 5,675,014 A | 10/1997 | Cohen et al. |
| 5,684,171 A | 11/1997 | Wideman et al. |
| 5,684,172 A | 11/1997 | Wideman et al. |
| 5,770,754 A | 6/1998 | Scholl |
| 5,834,536 A | 11/1998 | Scholl |
| 5,859,275 A | 1/1999 | Munzenberg et al. |
| 5,892,085 A | 4/1999 | Munzenbert et al. |
| 5,936,112 A | 8/1999 | Gobel et al. |
| 5,965,760 A * | 10/1999 | Michel et al. ............... 556/427 |
| 6,015,870 A * | 1/2000 | Ichinohe et al. .............. 528/30 |
| 6,066,752 A | 5/2000 | Takata et al. |
| 6,114,560 A * | 9/2000 | Ichinohe et al. ............. 556/427 |
| 6,423,859 B1 * | 7/2002 | Alig et al. .................. 556/427 |
| 2002/0049347 A1 | 4/2002 | Alig et al. |

FOREIGN PATENT DOCUMENTS

| EP | 0 773 224 A2 | 5/1997 |
| EP | 0 845 472 A2 | 6/1998 |
| EP | 0 894 803 A2 | 2/1999 |
| EP | 0 908 463 A2 * | 4/1999 |
| EP | 0 937 732 A2 | 8/1999 |
| EP | 0 963 995 A2 * | 12/1999 |
| EP | 1 172 367 A2 | 1/2002 |
| EP | 1 279 675 A2 | 1/2003 |
| JP | 9-169774 A | 6/1997 |
| JP | 11-100388 A | 4/1999 |
| WO | WO 01/74825 A1 | 10/2001 |

* cited by examiner

*Primary Examiner*—Johann Richter
*Assistant Examiner*—Chukwuma Nwaonicha
(74) *Attorney, Agent, or Firm*—Birch, Stewart, Kolasch & Birch, LLP

(57) ABSTRACT

By premixing a sulfide chain-bearing organosilicon compound, a halogenoalkyl group-bearing organosilicon compound, and optionally, sulfur, adding anhydrous sodium sulfide $Na_2S$ to the premix, and allowing reaction to take place, a sulfide chain-bearing organosilicon compound having a shorter sulfide chain can be prepared in high yields and at a lost cost while minimizing formation of monosulfide-bearing organosilicon compound.

5 Claims, No Drawings

PREPARATION OF SULFIDE CHAIN-BEARING ORGANOSILICON COMPOUNDS

FIELD OF THE INVENTION

This invention relates to a method for changing the sulfide chain distribution of a sulfide chain-bearing organosilicon compound having the following general formula (1):

$$(R^1O)_{(3-p)}(R^2)_p Si-R^3-S_m-R^3-Si(OR^1)_{(3-p)}(R^2)_p \quad (1)$$

wherein $R^1$ and $R^2$ each are a monovalent hydrocarbon group having 1 to 4 carbon atoms, $R^3$ is a divalent hydrocarbon group having 1 to 10 carbon atoms, m has an average value of $2<m\leq 6$, and p is 0, 1 or 2. More particularly, it relates to a method for converting a sulfide chain-bearing organosilicon compound having the formula (1) to a sulfide chain-bearing organosilicon compound having a shorter sulfide chain in a distribution having a minimized content of monosulfide-bearing organosilicon compound.

BACKGROUND OF THE INVENTION

In silica-loaded tires, bis-triethoxysilyltetrasulfide is widely used as a coupling agent between rubber and silica. However, when mixed with rubber and silica at elevated temperatures, this compound acts to increase the viscosity of the blend, which is inconvenient to subsequent operation.

To overcome this problem, shorter chain polysulfide compounds such as bis-triethoxysilylpropyldisulfide were proposed. For example, JP-A 9-169774 discloses a method for preparing disulfide silanes using NaCN. This method, however, has the problem of using the toxic compound. It would be desirable to have a substitute safe method of preparing short sulfide chain-bearing organosilicon compounds at low cost.

The inventors proposed in JP-A 11-100388 a method of preparing a short sulfide chain-bearing organosilicon compound by reacting a polysulfide silane of the general formula: $(RO)_3SiC_3H_6S_xC_3H_6Si(OR)_3$ wherein R is methyl or ethyl, and x is a positive number of 3 to 6 on the average, at least one anhydrous sulfur compound: $M^1{}_2S$ or $M^2S$ wherein $M^1$ is an alkali metal or ammonium and $M^2$ is an alkaline earth metal or zinc, and a halogenoalkoxysilane of the general formula: $XC_3H_6Si(OR)_3$ wherein X is halogen and R is methyl or ethyl. When the short sulfide chain-bearing organosilicon compound is prepared by this method, however, there can also be produced a monosulfide chain-bearing organosilicon compound, that is, an organosilicon compound having a sulfide chain which does not fully participate in the reactions with silica and rubber.

SUMMARY OF THE INVENTION

An object of the present invention is to provide a safe and economical method for preparing, from a sulfide chain-bearing organosilicon compound of the formula (1), a sulfide chain-bearing organosilicon compound having a shorter average sulfide chain and having a minimal content of monosulfide chain-bearing organosilicon compound in its composition.

In one aspect, the present invention provides a method for preparing a sulfide chain-bearing organosilicon compound, comprising the steps of:

premixing a sulfide chain-bearing organosilicon compound having the general formula (1):

$$(R^1O)_{(3-p)}(R^2)_p Si-R^3-S_m-R^3-Si(OR^1)_{(3-p)}(R^2)_p \quad (1)$$

wherein $R^1$ and $R^2$ each are a monovalent hydrocarbon group of 1 to 4 carbon atoms, $R^3$ is a divalent hydrocarbon group of 1 to 10 carbon atoms, m has an average value of $2<m\leq 6$, and p is 0, 1 or 2, a halogenoalkyl group-bearing organosilicon compound having the general formula (2):

$$(R^1O)_{(3-p)}(R^2)_p Si-R^3-X \quad (2)$$

wherein $R^1$ and $R^2$ each are a monovalent hydrocarbon group of 1 to 4 carbon atoms, $R^3$ is a divalent hydrocarbon group of 1 to 10 carbon atoms, X is a halogen atom, and p is 0, 1 or 2, and optionally, sulfur, adding anhydrous sodium sulfide represented by $Na_2S$ to the premix, and allowing reaction to take place for thereby forming a sulfide chain-bearing organosilicon compound having the general formula (3):

$$(R^1O)_{(3-p)}(R^2)_p Si-R^3-S_n-R^3-Si(OR^1)_{(3-p)}(R^2)_p \quad (3)$$

wherein $R^1$ and $R^2$ each are a monovalent hydrocarbon group of 1 to 4 carbon atoms, $R^3$ is a divalent hydrocarbon group of 1 to 10 carbon atoms, n has an average value of $2\leq n<6$, satisfying m>n, and p is 0, 1 or 2, while minimizing formation of a monosulfide-bearing organosilicon compound with n=1.

In another aspect, the present invention provides a method for preparing a sulfide chain-bearing organosilicon compound, comprising the steps of:

preforming a sulfide chain-bearing organosilicon compound having the general formula (1):

$$(R^1O)_{(3-p)}(R^2)_p Si-R^3-S_m-R^3-Si(OR^1)_{(3-p)}(R^2)_p \quad (1)$$

wherein $R^1$ and $R^2$ each are a monovalent hydrocarbon group of 1 to 4 carbon atoms, $R^3$ is a divalent hydrocarbon group of 1 to 10 carbon atoms, m has an average value of $2<m\leq 6$, and p is 0, 1 or 2, from anhydrous sodium sulfide represented by $Na_2S$, sulfur, and a halogenoalkyl group-bearing organosilicon compound having the general formula (2):

$$(R^1O)_{(3-p)}(R^2)_p Si-R^3-X \quad (2)$$

wherein $R^1$ and $R^2$ each are a monovalent hydrocarbon group of 1 to 4 carbon atoms, $R^3$ is a divalent hydrocarbon group of 1 to 10 carbon atoms, X is a halogen atom, and p is 0, 1 or 2, if necessary, combining the sulfide chain-bearing organosilicon compound of formula (1) with the halogenoalkyl group-bearing organosilicon compound of formula (2) and optionally, sulfur, adding anhydrous sodium sulfide represented by $Na_2S$ to the sulfide chain-bearing organosilicon compound of formula (1), and allowing reaction to take place for thereby forming a sulfide chain-bearing organosilicon compound having the general formula (3):

$$(R^1O)_{(3-p)}(R^2)_p Si-R^3-S_n-R^3-Si(OR^1)_{(3-p)}(R^2)_p \quad (3)$$

wherein $R^1$ and $R^2$ each are a monovalent hydrocarbon group of 1 to 4 carbon atoms, $R^3$ is a divalent hydrocarbon group of 1 to 10 carbon atoms, n has an average value of $2\leq n<6$, satisfying m>n, and p is 0, 1 or 2, while minimizing formation of a monosulfide-bearing organosilicon compound with n=1.

With this method, the desired sulfide chain-bearing organosilicon compound, and especially a sulfide chain-bearing organosilicon compound of formula (3) wherein n has an average value of 2 to 3 is produced in high yields while minimizing the content of monosulfide-bearing organosilicon compound of formula (3) wherein n=1.

DESCRIPTION OF THE PREFERRED EMBODIMENTS

Briefly stated, according to the invention, by premixing a sulfide chain-bearing organosilicon compound of formula (1), a halogenoalkyl group-bearing organosilicon compound of formula (2), and optionally, sulfur, adding anhydrous sodium sulfide represented by $Na_2S$ thereto, and allowing reaction to take place, a sulfide chain-bearing organosilicon compound of formula (3) is obtained while minimizing formation of monosulfide-bearing organosilicon compound of formula (3) wherein n=1.

One starting reactant is a sulfide chain-bearing organosilicon compound having the average compositional formula (1).

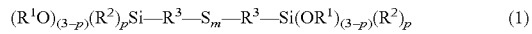

In the formula, $R^1$ and $R^2$ are independently selected from monovalent hydrocarbon groups having 1 to 4 carbon atoms, for example, alkyl and alkenyl groups such as methyl, ethyl, n-propyl, i-propyl, n-butyl, i-butyl, t-butyl, allyl and methallyl. $R^3$ is selected from divalent hydrocarbon groups having 1 to 10 carbon atoms, for example, alkylene, arylene and alkenylene groups and combinations thereof, such as methylene, ethylene, propylene, n-butylene, i-butylene, hexylene, decylene, phenylene, and methylphenylethylene, and combinations thereof. The subscript m has an average value of $2<m\leq6$ and preferably $3\leq m\leq4$, and p is equal to 0, 1 or 2, preferably 0 or 1, most preferably 0.

Typical examples of the compound of formula (1) are given below.

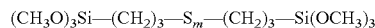

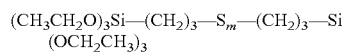

In the above-described compounds, S has a distribution partially because of disproportionation reaction, so that its number (m) is described essentially as an average value. In formula (1), m has an average value of $2<m\leq6$ and preferably $3\leq m\leq4$.

The halogenoalkyl group-bearing organosilicon compound used herein has the following general formula (2).

In the formula, $R^1$, $R^2$, $R^3$ and p are as defined above, and X is a halogen atom such as Cl, Br or I, preferably Cl or Br.

Typical examples of the compound of formula (2) are given below.

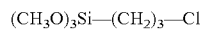

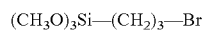

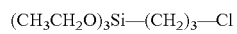

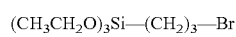

When the reaction is conducted, sulfur is added if desired for adjusting the length of sulfide chain. It is not preferred to add a large amount of sulfur because the resulting product contains more monosulfide chain-bearing organosilicon compound.

According to the invention, the compounds of formulae (1) and (2) and optionally, sulfur are mixed, and anhydrous sodium sulfide represented by $Na_2S$ is then added to the mixture whereupon reaction is carried out.

The use of a solvent is optional when the end compound is prepared according to the invention. A solventless system is acceptable. Examples of the solvent, if used, include aliphatic hydrocarbons such as pentane, hexane, heptane and octane, aromatic hydrocarbons such as benzene, toluene and xylene, alcohols such as methanol and ethanol, and ethers such as diethyl ether, dibutyl ether, tetrahydrofuran and dioxane. Of these, the ethers such as dibutyl ether, tetrahydrofuran and dioxane and the alcohols such as methanol and ethanol are preferred.

In a preferred embodiment, the compounds of formulae (1) and (2) and optional sulfur are mixed in a solvent, and $Na_2S$ is gradually added to the mixture for reaction to take place; and the reaction mixture is ripened following the addition of $Na_2S$.

The reaction temperature is not critical and generally ranges from room temperature to about 200° C., and preferably from about 60° C. to about 170° C. The reaction time is usually about 30 minutes or more. The reaction proceeds to completion within about 2 hours to about 15 hours.

With respect to the molar ratio of the compound of average compositional formula (1) to $Na_2S$, the $Na_2S$ may be added in accordance with the desired value of n in the average compositional formula (3). Most often the compound of formula (2) may be added in an equimolar amount to Na in the $Na_2S$ added. It is noted that the system becomes alkaline as the moles of the compound of formula (2) decreases, and becomes nearly neutral as the moles of the compound of formula (2) increases. More illustratively, when reaction is made among 1 mole of the compound of average compositional formula (1) wherein m has an average value of 4, 1 mole of $Na_2S$ and 2 moles of the compound of formula (2), there is obtained a compound of average compositional formula (3) wherein n has an average value of 2.5. When the solvent is used, it may be distilled off in vacuum at the end of reaction and before or after the salt formed is separated by filtration.

The compound of average compositional formula (1) used herein may be a previously isolated one. Alternatively, in the same reactor as used for the reaction, a sulfide chain-bearing organosilicon compound of average compositional formula (1) is previously formed from sodium sulfide $Na_2S$, sulfur, and a halogenoalkyl group-bearing organosilicon compound of formula (2). Thereafter, the halogenoalkyl group-bearing organosilicon compound of formula (2) and optionally, sulfur are added and mixed therewith, if necessary, and $Na_2S$ is added for reaction to take place whereby the sulfide chain-bearing organosilicon compound of average compositional formula (3) is obtained.

In the alternative procedure, when the compound of average compositional formula (1) is preformed, the order of addition of $Na_2S$, the organosilicon compound of formula (2) and sulfur is arbitrary. In the step of preforming the compound of average compositional formula (1), the compound of formula (2) and sulfur may be added in amounts that include their amounts to be added later.

The use of a solvent is optional when the compound of formula (1) is preformed. A solventless system is acceptable.

Examples of the solvent, if used, include aliphatic hydrocarbons such as pentane and hexane, aromatic hydrocarbons such as benzene, toluene and xylene, ethers such as tetrahydrofuran, diethyl ether and dibutyl ether, and alcohols such as methanol and ethanol. Of these, the ethers such as tetrahydrofuran and the alcohols such as methanol and ethanol are preferred.

The reaction temperature in the preforming step is not critical and generally ranges from room temperature to about 200° C., and preferably from about 60° C. to about 170° C. The reaction time is usually about 30 minutes or more. The reaction proceeds to completion within about 30 minutes to about 8 hours, allowing progress to the subsequent reaction.

Once the compound of formula (1) is obtained through the above reaction, $Na_2S$ is added thereto for reaction to take place to produce the compound of formula (3) in the same way and under the same conditions as described above.

The thus obtained compound has the average compositional formula (3).

$$(R^1O)_{(3-p)}(R^2)_pSi-R^3-S_n-R^3-Si(OR^1)_{(3-p)}(R^2)_p \quad (3)$$

In the formula, $R^1$ and $R^2$ each are a monovalent hydrocarbon group having 1 to 4 carbon atoms, and $R^3$ is a divalent hydrocarbon group having 1 to 10 carbon atoms, examples of which are as illustrated in conjunction with formula (1). The subscript p is 0, 1 or 2. The subscript n has an average value of $2 \leq n < 6$, and is smaller than m in formula (1), i.e., m>n, and preferably has an average value of $2 \leq n \leq 3$, exclusive of m=n=3. In the compound (mixture) obtained by the inventive method, the formation of the compound of formula (3) wherein n=1 is minimized, to a level of at most 5 mol %, preferably at most 2 mol %, and especially at most 1 mol %.

Typical examples of the compound of formula (3) are given below.

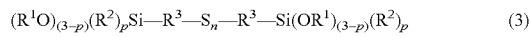

$(CH_3O)_3Si-(CH_2)_3-S_n-(CH_2)_3-Si(OCH_3)_3$ $(CH_3CH_2O)_3Si-(CH_2)_3-S_n-(CH_2)_3-Si(OCH_2CH_3)_3$ $(CH_3CH_2O)_3Si-CH_2CH(CH_3)CH_2-S_n-CH_2CH(CH_3)CH_2-Si(OCH_2CH_3)_3$

EXAMPLE

Examples of the invention are given below by way of illustration and not by way of limitation.

Example 1

A 1-liter separable flask equipped with a nitrogen gas inlet, thermometer, Dimroth condenser and dropping funnel was charged with 300 g of ethanol, 269 g (0.5 mol) of bis-triethoxysilylpropyltetrasulfide, and 240.5 g (1.0 mol) of 3-chloropropyltriethoxysilane and heated at 70° C. To the flask, 39 g (0.5 mol) of anhydrous sodium sulfide was gradually added over 10 minutes. At the end of addition, the reaction mixture was ripened for 8 hours. The solution was then filtered. The filtrate was concentrated in vacuum in a rotary evaporator, yielding 437 g of a brown clear liquid. On analysis by infrared (IR) absorption spectroscopy and proton nuclear magnetic resonance ($^1$H-NMR) spectroscopy and sulfur content determination, it was confirmed to be a sulfide group-bearing alkoxysilane of the following average compositional formula.

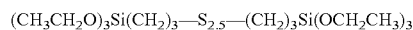

$(CH_3CH_2O)_3Si(CH_2)_3-S_{2.5}-(CH_2)_3Si(OCH_2CH_3)_3$

To confirm the sulfide distribution of the compound, supercritical chromatography was carried out. Its sulfide silane distribution (mol %) is shown below.

| | |
|---|---|
| n = 1 | 0.5% |
| n = 2 | 56.6% |
| n = 3 | 30.5% |
| n = 4 | 10.3% |
| n = 5 | 2.1% |
| n = 6 | ≦0.1% |

The bis-triethoxysilylpropyltetrasulfide used as the starting reactant had the sulfide silane distribution (mol %) shown below.

| | |
|---|---|
| m = 1 | 0.1% |
| m = 2 | 18.7% |
| m = 3 | 30.3% |
| m = 4 | 24.6% |
| m = 5 | 16.1% |
| m = 6 | 6.2% |
| m = 7 | 3.1% |
| m = 8 | 1.0% |

Example 2

A 2-liter separable flask equipped with a nitrogen gas inlet, thermometer, Dimroth condenser and dropping funnel was charged with 500 g of ethanol, 39 g (0.5 mol) of anhydrous sodium sulfide, and 48 g (1.5 mol) of sulfur and heated at 70° C. To the flask, 240.5 g (1.0 mol) of 3-chloropropyltriethoxysilane was slowly added dropwise over 30 minutes. At the end of addition, the reaction mixture was ripened for 2 hours. The solution was cooled to 35° C., and 240.5 g (1.0 mol) of 3-chloropropyltriethoxysilane was added thereto. The solution was heated at 70° C., after which 39 g (0.5 mol) of anhydrous sodium sulfide was gradually added over 10 minutes. At the end of addition, the reaction mixture was ripened for 8 hours. The solution was then filtered. The filtrate was concentrated in vacuum in a rotary evaporator, yielding 433 g of a brown clear liquid. On analysis by IR and $^1$H-NMR spectroscopy and sulfur content determination, it was confirmed to be a sulfide group-bearing alkoxysilane of the following average compositional formula, as in Example 1.

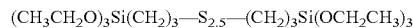

$(CH_3CH_2O)_3Si(CH_2)_3-S_{2.5}-(CH_2)_3Si(OCH_2CH_3)_3$

To confirm the sulfide distribution of the compound, supercritical chromatography was carried out. Its sulfide silane distribution (mol %) is shown below.

| | |
|---|---|
| n = 1 | 0.7% |
| n = 2 | 55.4% |
| n = 3 | 31.5% |
| n = 4 | 10.4% |
| n = 5 | 2.0% |
| n = 6 | ≦0.1% |

Example 3

A 2-liter separable flask equipped with a nitrogen gas inlet, thermometer, Dimroth condenser and dropping funnel was charged with 500 g of ethanol, 39 g (0.5 mol) of anhydrous sodium sulfide, and 40.0 g (1.25 mol) of sulfur and heated at 70° C. To the flask, 481.0 g (2.0 mol) of 3-chloropropyltriethoxysilane was slowly added dropwise over 45 minutes. At the end of addition, the reaction mixture was ripened for 2 hours. To the solution, 39 g (0.5 mol) of anhydrous sodium sulfide was gradually added over 10 minutes. At the end of addition, the reaction mixture was ripened for 8 hours. The solution was then filtered. The filtrate was concentrated in vacuum in a rotary evaporator, yielding 448 g of a brown clear liquid. On analysis by IR and $^1$H-NMR spectroscopy and sulfur content determination, it was confirmed to be a sulfide group-bearing alkoxysilane of the following average compositional formula.

$(CH_3CH_2O)_3Si(CH_2)_3—S_{2.25}—(CH_2)_3Si(OCH_2CH_3)_3$

To confirm the sulfide distribution of the compound, supercritical chromatography was carried out. Its sulfide silane distribution (mol %) is shown below.

| | |
|---|---|
| n = 1 | 0.7% |
| n = 2 | 71.5% |
| n = 3 | 22.7% |
| n = 4 | 4.2% |
| n = 5 | 0.9% |
| n = 6 | ≦0.1% |

Comparative Example 1

A 2-liter separable flask equipped with a nitrogen gas inlet, thermometer, Dimroth condenser and dropping funnel was charged with 300 g of ethanol, 269 g (0.5 mol) of bis-triethoxysilylpropyltetrasulfide, and 39.0 g (0.5 mol) of anhydrous sodium sulfide. Reaction was conducted at 80° C. for 1 hour. Thereafter, 240.5 g (1.0 mol) of 3-chloropropyltriethoxysilane was added dropwise over 30 minutes. After the completion of dropwise addition, the reaction solution was ripened for 8 hours. The solution was filtered. The filtrate was concentrated in vacuum in a rotary evaporator, yielding 434 g of a brown clear liquid. On analysis by IR and $^1$H-NMR spectroscopy and sulfur content determination, it was confirmed to be a sulfide group-bearing alkoxysilane of the following average compositional formula, as in Example 1.

$(CH_3CH_2O)_3Si(CH_2)_3—S_{2.5}—(CH_2)_3Si(OCH_2CH_3)_3$

To confirm the sulfide distribution of the compound, supercritical chromatography was carried out. Its sulfide silane distribution (mol %) is shown below.

| | |
|---|---|
| n = 1 | 2.1% |
| n = 2 | 55.4% |
| n = 3 | 29.8% |
| n = 4 | 10.2% |
| n = 5 | 2.5% |
| n = 6 | ≦0.1% |

Comparative Example 2

A 2-liter separable flask equipped with a nitrogen gas inlet, thermometer, Dimroth condenser and dropping funnel was charged with 500 g of ethanol, 78 g (1.0 mol) of anhydrous sodium sulfide and 40.0 g (1.25 mol) of sulfur and heated at 70° C. Reaction was conducted for 1 hour. Thereafter, 481.0 g (2.0 mol) of 3-chloropropyltriethoxysilane was slowly added dropwise over 45 minutes. After the completion of dropwise addition, the reaction solution was ripened for 8 hours. The solution was filtered. The filtrate was concentrated in vacuum in a rotary evaporator, yielding 440 g of a brown clear liquid. On analysis by IR and $^1$H-NMR spectroscopy and sulfur content determination, it was confirmed to be a sulfide group-bearing alkoxysilane of the following average compositional formula, as in Example 3.

$(CH_3CH_2O)_3Si(CH_2)_3—S_{2.25}—(CH_2)_3Si(OCH_2CH_3)_3$

To confirm the sulfide distribution of the compound, supercritical chromatography was carried out. Its sulfide silane distribution (mol %) is shown below.

| | |
|---|---|
| n = 1 | 7.3% |
| n = 2 | 60.8% |
| n = 3 | 24.1% |
| n = 4 | 6.4% |
| n = 5 | 1.4% |
| n = 6 | ≦0.1% |

According to the invention, from a sulfide chain-bearing organosilicon compound of the formula (1), a polysulfidesilane having a shorter polysulfide chain can be prepared in high yields and at a low cost. The resulting compound is of a composition having a low content of monosulfide chain-bearing organosilicon compound which is less reactive with rubber, and thus useful in the industry, typically as additives to silica-loaded tire rubber compositions.

Japanese Patent Application No. 2002-062900 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a sulfide chain-bearing organosilicon compound, comprising the steps of:
   premixing a sulfide chain-bearing organosilicon compound having the general formula (1):

$(R^1O)_{(3-p)}(R^2)_pSi—R^3—S_m—R^3—Si(OR^1)_{(3-p)}(R^2)_p$     (1)

wherein $R^1$ and $R^2$ each are a monovalent hydrocarbon group of 1 to 4 carbon atoms, $R^3$ is a divalent hydrocarbon group of 1 to 10 carbon atoms, m has an average value of 3 to 4, and p is 0, 1 or 2, with a halogenoalkyl group-bearing organosilicon compound having the general formula (2):

$(R^1O)_{(3-p)}(R^2)_pSi—R^3—X$     (2)

wherein $R^1$ and $R^2$ each are a monovalent hydrocarbon group of 1 to 4 carbon atoms, $R^3$ is a divalent hydrocarbon group of 1 to 10 carbon atoms, X is a halogen atom, and p is 0, 1 or 2, and sulfur,
   adding anhydrous sodium sulfide represented by $Na_2S$ to the premix, and
   allowing reaction to take place for thereby forming a sulfide chain-bearing organosilicon compound having the general formula (3):

$(R^1O)_{(3-p)}(R^2)_pSi—R^3—S_n—R^3—Si(OR^1)_{(3-p)}(R^2)_p$     (3)

wherein $R^1$ and $R^2$ each are a monovalent hydrocarbon group of 1 to 4 carbon atoms, $R^3$ is a divalent hydrocarbon group of 1 to 10 carbon atoms, n has an average value 2 to 3, exclusive of m=n=3, and p is 0, 1 or 2, while minimizing formation of a monosulfide-bearing organosilicon compound with n=1 to a level of at most 1 mol %.

2. A method for preparing a sulfide chain-bearing organosilicon compound, comprising the steps of:

preforming a sulfide chain-bearing organosilicon compound having the general formula (1):

$$(R^1O)_{(3-p)}(R^2)_p Si\text{—}R^3\text{—}S_m\text{—}R^3\text{—}Si(OR^1)_{(3-p)}(R^2)_p \quad (1)$$

wherein $R^1$ and $R^2$ each are a monovalent hydrocarbon group of 1 to 4 carbon atoms, $R^3$ is a divalent hydrocarbon group of 1 to 10 carbon atoms, m has an average value of 3 to 4, and p is 0, 1 or 2, from anhydrous sodium sulfide represented by $Na_2S$, sulfur, and a halogenoalkyl group-bearing organosilicon compound having the general formula (2):

$$(R^1O)_{(3-p)}(R^2)_p Si\text{—}R^3\text{—}X \quad (2)$$

wherein $R^1$ and $R^2$ each are a monovalent hydrocarbon group of 1 to 4 carbon atoms, $R^3$ is a divalent hydrocarbon group of 1 to 10 carbon atoms, X is a halogen atom, and p is 0, 1 or 2, if necessary, combining the sulfide chain-bearing organosilicon compound of formula (1) with the halogenoalkyl group-bearing organosilicon compound of formula (2) and sulfur, adding anhydrous sodium sulfide represented by $Na_2S$ to the sulfide chain-bearing organosilicon compound of formula (1), and allowing reaction to take place thereby forming a sulfide chain-bearing organosilicon compound having the general formula (3):

$$(R^1O)_{(3-p)}(R^2)_p Si\text{—}R^3\text{—}S_n\text{—}R^3\text{—}Si(OR^1)_{(3-p)}(R^2)_p \quad (3)$$

wherein $R^1$ and $R^2$ each are a monovalent hydrocarbon group of 1 to 4 carbon atoms, $R^3$ is a divalent hydrocarbon group of 1 to 10 carbon atoms, n has an average value 2 to 3, exclusive of m=n=3, and p is 0, 1 or 2, while minimizing formation of a monosulfide-bearing organosilicon compound with n=1 to a level of at most 1 mol %.

3. The method of claim 1, wherein the halogenoalkyl group-bearing compound 3-chloropropyltriethoxysilane is premixed with bis-triethoxysilylpropyltetrasulfide and then reacted with sodium sulfide to produce a compound of the formula $(CH_3CH_2O)_3Si(CH_2)_3\text{—}S_{2.5}\text{—}(CH_2)_3Si(OCH_2CH_3)_3$.

4. The method of claim 2, wherein the halogenoalkyl group-bearing compound 3-chloropropyltriethoxysilane is reacted with sulfur and sodium sulfide to form an intermediate reaction product mixture, additional 3-chloropropyltriethoxysilane is added to the intermediate reaction product to form a second intermediate reaction product mixture, and the second intermediate reaction mixture is reacted with sodium sulfide to produce a compound of the formula $(CH_3CH_2O)_3Si(CH_2)_3\text{—}S_{2.5}\text{—}(CH_2)_3Si(OCH_2CH_3)_3$.

5. The method of claim 2, wherein the halogenoalkyl group-bearing compound 3-chloropropyltriethoxysilane is reacted with sulfur and sodium sulfide to form an intermediate reaction product and the resulting intermediate reaction product is reacted with sodium sulfide to produce a compound of the formula $(CH_3CH_2O)_3Si(CH_2)_3\text{—}S_{2.25}\text{—}(CH_2)_3Si(OCH_2CH_3)_3$.

* * * * *